(12) United States Patent
Huang et al.

(10) Patent No.: US 8,710,294 B2
(45) Date of Patent: Apr. 29, 2014

(54) TRANSPARENT ZEBRAFISH AND PREPARATION METHOD THEREOF

(75) Inventors: Wei-Chang Huang, Hsinchu (TW); Yung-Jen Chuang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 13/026,634

(22) Filed: Feb. 14, 2011

(65) Prior Publication Data
US 2012/0210449 A1 Aug. 16, 2012

(51) Int. Cl.
*A01K 67/027* (2006.01)
*G01N 33/00* (2006.01)

(52) U.S. Cl.
CPC ........... *A01K 67/027* (2013.01); *A01K 2217/15* (2013.01); *A01K 2267/00* (2013.01); *A01K 2227/40* (2013.01)
USPC .................................. 800/20; 800/22; 800/3

(58) Field of Classification Search
CPC ............ A01K 2217/15; A01K 67/027; A01K 2227/40
USPC ................................................. 800/3, 18, 20
See application file for complete search history.

(56) References Cited

PUBLICATIONS

John F. Rawls et al., How the Zebrafish Gets Its Stripes, Developomental Biology, 2001, pp. 301-314, vol. 240.
Richard Mark White et al., Transparent Adult Zebrafish as a Tool for In Vivo Transplantation Analysis, Cell Stem Cell, Feb. 2008, pp. 183-189, vol. 2.
David M. Langenau et al., Myc-Induced T Cell Leukemia in Transgenic Zebrafish, Science, Feb. 7, 2003, pp. 887-890, vol. 299.
James F. Amatruda et al., Zebrafish as a cancer model system, Cancer Cell, Apr. 2002, pp. 229-231.
David Traver et al., Transplantation and in vivo imaging of multilineage engraftment in zebrafish bloodless mutants, Nature Immunology, Dec. 2003, pp. 1238-1246, vol. 4, No. 12.
Stefania Nicoli et al., Mammalian Tumor Xenografts Induce Neovascularization in Zebrafish Embryos, Cancer Research, Apr. 4, 2007, pp. 2927-2931, vol. 67, No. 7.
Timothy J.A. Chico et al., Modeling Cardiovascular Disease in the Zebrafish, Trends Cardiovasc Med, 2008, pp. 150-155, vol. 18, No. 4.
Shuji Kishi et al., The zebrafish as a vertebrate model of functional aging and very gradual senescence, Experimental Gerontology, 2003, pp. 777-786, vol. 38.
Jonathan Cachat et al., Measuring behavioral and endocrine responses to novelty stress in adult zebrafish, Natural Protocols, 2010, pp. 1786-1799, vol. 5, No. 11.
Youngsup Song et al., Creation of a genetic model of obesity in a teleost, The FASEB Journal, 2007, pp. 2042-2049, vol. 21, No. 9.
T. Cameron Tran et al., Automated, Quantitative Screening Assay for Antiangiogenic Compounds Using Transgenic Zebrafish, Cancer Research, Dec. 1, 2007, pp. 11386-11392, vol. 67, No. 23.
Peter M. Eimon et al., The use of in vivo zebrafish assays in drug toxicity screening, Expert Opin. Drug Metab. Toxicol., 2009, pp. 393-401, vol. 5, No. 4.
J. Muse Davis et al., The Role of the Granuloma in Expansion and Dissemination of Early Tuberculosis Infection, Cell, Jan. 9, 2009, pp. 37-49, vol. 136.
C. A. Byrd et al., Neurogenesis in the Olfactory Bulb of Adult Zebrafish, Neuroscience, 2001, pp. 793-801, vol. 105, No. 4.
Subhra Prakash Hui et al., Cellular Response After Crush Injury in Adult Zebrafish Spinal Cord, Developmental Dynamics, 2010, pp. 2962-2979, vol. 239.
Thomas S. Vihtelic et al., Light-Induced Rod and Cone Cell Death and Regeneration in the Adult albino Zebrafish (*Danio rerio*) Retina, J Neurobiol, 2000, pp. 289-307, vol. 44.
Kenneth D. Poss et al., Heart Regeneration in Zebrafish, Science, Dec. 13, 2002, pp. 2188-2190, vol. 298.
German Poleo et al., Cell Proliferation and Movement During Early Fin Regeneration in Zebrafish, Developmental Dynamics, 2001, pp. 380-390, vol. 221.
Maryann Haldi et al., Human melanoma cells transplanted into zebrafish proliferate, migrate, produce melanin, form masses and stimulate angiogenesis in zebrafish, Angiogenesis, 2006, pp. 139-151, vol. 9.
John A. Byers, Analysis of Insect and Plant Colors in Digital Images Using Java Software on the Internet, Annals of the Entomological Society of America, 2006, pp. 865-874, vol. 99, No. 5.

*Primary Examiner* — Valarie Bertoglio
(74) *Attorney, Agent, or Firm* — WPAT, P.C.; Anthony King; Kay Yang (57) ABSTRACT

This invention provides a biological selective breeding technique in preparation of a transparent zebrafish, Citrine. The appearance of Citrine is transparent and yellowish, with uniformly pigmented black eyes and its inner organs are observable by eyes. The invention also provides a method for in vivo observation of progression and expansion of various disease stages or physiological processes.

1 Claim, 6 Drawing Sheets
(5 of 6 Drawing Sheet(s) Filed in Color)

FIG. 3 citrine.jpg  (132,156)-(1077,241)  N = 946 x 86 = 81356
R = 165 ± 56 (34%)  G = 141 ± 54 (38%)  B = 105 ± 41 (38%)

Red% = 40.1 ± 13.7%   Green% = 34.3 ± 13.2%   Blue% = 25.5 ± 9.9%
Red CV = 34.2%   Green CV = 38.5%   Blue CV = 38.8%

WT.jpg  (134,128)-(1118,227)  N = 985 x 100 = 98500
R = 159 ± 58 (36%)  G = 167 ± 54 (32%)  B = 167 ± 56 (34%)

Red% = 32.3 ± 11.7%   Green% = 33.9 ± 10.9%   Blue% = 33.9 ± 11.4%
Red CV = 36.2%   Green CV = 32.2%   Blue CV = 33.6%

SEQUENCE LISTING

```
<160> NUMBER OF SEQ ID NOS: 2

<210> SEQ ID NO 1
<211> LENGTH: 1565
<212> TYPE: DNA
<213> ORGANISM: Danio rerio
<220> FEATURE:
<221> NAME/KEY: promoter
<222> LOCATION: (1)..(1565)

<400> SEQUENCE: 1
ctcgagtgac caaagcttaa atcagttgtg ttaaataaga gacattcaaa ataaatgtaa      60
atgagctctc caaatcagca gacttaacat tctttaaaat gattgattca atagtgataa     120
aaatcaggca tagccagttg taactttaga taaattacag aaaatgtcaa atacagagaa     180
ccgattcttt tttatgatac atccaagcac acatttaaca caatccaggc aaaccccgaa     240
tttcacagtc acaagcactg tttgtacaag agctttgcct aaggacacac agtctctata     300
agtccaggtc gttggtttca ctcttatttt aaacatgtga cattttcct gccatcctgt      360 cttaggctgc tgtttgcttc attccatgtc acattaattt cctcagtagc accttttaca     420
cacacagcca atctttccca gaaaattcaa ttgctttgaa aagataatgt gtgaacaaat     480
ccatttagaa aaggaaaatt aagaatttgt aaaatcatct gtaaattgtt ggcattcttc     540
tgtatatgaa catcacatca tttacaggta aaggtctggt cattaattat atgacaattt     600
actggtatta ttttgtgaaa ggggctattt tcaatgcatt catccatcct tttcatccct     660
caaatctctc attcacgtcc ccctcccat ctgcacactt tatctcattt tccaccctgc      720
tggaatctga gcacttgtgc agttatcagg gctcctgtat ttaggaggct ctgggtgtcc     780
atgtagggga cgaacagaaa cactgcagac ctttatagaa gaacaaatga taagagtcct     840
catacataaa gactccatta gaaacgtcag tgacccagga gcccagacca acagcaaagc     900
agacagtgaa catggtgagt agacaaagct atactttttt ggttttgaat ataatattaa     960
tgtgaaaata aaaagcgtct atatgaagtt aaattgtatg ttgtgatact atctttttaat   1020 gagtattttt acttaggtac tttttttctgt acactgtaaa acgcaaaaaa gttaaggtaa    1080
ctcaaatcat ttgagaaaac cgattgtaac aagccatctg aagttcaaaa actaatctaa   1140
```

| | | |
|---|---|---|
| atgagtactg tgaacttaat ctatttgagt aaaagaagca atttgagcac agtaaaaccc | 1200 |
| agtaaatgaa gagaactcaa ccaactgagt actgtaaaac ccaataagat gaggcagctc | 1260 |
| acaccgtttg aggaaaccga ttgctacaaa ccatttgagt taaaaaaaaa gaatcaatat | 1320 |
| gagtactgtg aacttactcc atttaagttg aagtaatgag gtaattaatt aactcattac | 1380 |
| cctcaacact gagttcaaaa ctcttttcaa atgagtagaa ttaattttca gccaattttg | 1440 |
| agttaactat actcatttca tttgataaag ttgactattg ggttttacag tgtataaatg | 1500 |
| ctataaattg agtttccaaa taaggcttct ctttttttt actcacaggc tagtaaaaaa | 1560 |
| gccgc | 1565 |

<210> SEQ ID NO 2
<211> LENGTH: 6605
<212> TYPE: DNA
<213> ORGANISM: Danio rerio

<400> SEQUENCE: 2

| | | |
|---|---|---|
| ctttcctgcg ttatccctg attctgtgga taaccgtatt accgcctttg agtgagctga | 60 |
| taccgctcgc cgcagccgaa cgaccgagcg cagcgagtca gtgagcgagg aagcggaaga | 120 |
| gcgcccaata cgcaaaccgc ctctccccgc gcgttggccg attcattaat gcagctggca | 180 |
| cgacaggttt cccgactgga aagcgggcag tgagcgcaac gcaattaata cgcgtaccgc | 240 |
| tagccaggaa gagtttgtag aaacgcaaaa aggccatccg tcaggatggc cttctgctta | 300 |
| gtttgatgcc tggcagttta tggcgggcgt cctgcccgcc accctccggg ccgttgcttc | 360 |
| acaacgttca atccgctcc cggcggattt gtcctactca ggagagcgtt caccgacaaa | 420 |
| caacagataa acgaaaggc ccagtcttcc gactgagcct ttcgttttat ttgatgcctg | 480 |
| gcagttccct actctcgcgt taacgctagc atggatgttt cccagtcac gacgttgtaa | 540 |
| aacgacggcc agtcttaagc tcgggcccca aataatgatt ttattttgac tgatagtgac | 600 |
| ctgttcgttg caacacattg atgagcaatg cttttttata atgccaactt tgtacaaaaa | 660 |
| agcaggctac accatggctc caagaagaa gcgtaaggta atggtgagca agggcgagga | 720 |
| ggacaacatg gccatcatca aggagttcat gcgcttcaag gtgcacatgg agggctccgt | 780 |
| gaacggccgc gagttcgaga tcgagggcga gggcgagggc cgcccctacg agggcaccca | 840 |
| gaccgccaag ctgaaggtga ccaagggcgg cccctgccc ttcgcctggg acatcctgtc | 900 |
| ccctcagttc atgtacggct ccaaggccta cgtgaagcac cccgccgaca tccccgacta | 960 |
| cttgaagctg tccttccccg agggcttcaa gtgggagcgc gtgatgaact tcgaggacgg | 1020 |
| cggcgtggtg accgtgaccc aggactcctc cctgcaggac ggcgagttca tctacaaggt | 1080 |
| gaagctgcgc ggcaccaact tcccctccga cggccccgta atgcagaaga gaccatgggg | 1140 |
| ctggaggcc tcctccgagc ggatgtaccc cgaggacggc gccctgaagg gcagatcaa | 1200 |
| gcagaggctg aagctgaagg acggcggcca ctacgacgcc gaggtcaaga ccacctacaa | 1260 |
| ggccaagaag cccgtgcagc tgcccggcgc ctacaacgtc aacatcaagc tggacatcac | 1320 |
| ctcccacaac gaggactaca ccatcgtgga acagtacgag cgcgccgagg ccgccactc | 1380 |
| caccggcggc atggacgagc tgtacaagta agacccagct ttcttgtaca agttggcat | 1440 |
| tataagaaag cattgcttat caatttgttg caacgaacag gtcactatca gtcaaaataa | 1500 |
| aatcattatt tgccatccag ctgatatccc ctatagtgag tcgtattaca tggtcatagc | 1560 |
| tgtttcctgg cagctctggc ccgtgtctca aaatctctga tgttacattg cacaagataa | 1620 |
| aataatatca tcatgaacaa taaaactgtc tgcttacata aacagtaata caaggggtgt | 1680 |

```
tatgagccat attcaacggg aaacgtcgag gccgcgatta aattccaaca tggatgctga    1740
tttatatggg tataaatggg ctcgcgataa tgtcgggcaa tcaggtgcga caatctatcg    1800
cttgtatggg aagcccgatg cgccagagtt gtttctgaaa catggcaaag gtagcgttgc    1860
caatgatgtt acagatgaga tggtcagact aaactggctg acggaattta tgcctcttcc    1920
gaccatcaag cattttatcc gtactcctga tgatgcatgg ttactcacca ctgcgatccc    1980
cggaaaaaca gcattccagg tattagaaga atatcctgat tcaggtgaaa atattgttga    2040
tgcgctggca gtgttcctgc gccggttgca ttcgattcct gtttgtaatt gtccttttaa    2100
cagcgatcgc gtatttcgtc tcgctcaggc gcaatcacga atgaataacg gtttggttga    2160
tgcgagtgat tttgatgacg agcgtaatgg ctggcctgtt gaacaagtct ggaaagaaat    2220
gcataaactt ttgccattct caccggattc agtcgtcact catggtgatt tctcacttga    2280
taaccttatt tttgacgagg ggaaattaat aggttgtatt gatgttggac gagtcggaat    2340
cgcagaccga taccaggatc ttgccatcct atggaactgc ctcggtgagt tttctccttc    2400
attacagaaa cggcttttc aaaaatatgg tattgataat cctgatatga ataaattgca    2460
gtttcatttg atgctcgatg agttttctta atcagaattg gttaattggt tgtaacactg    2520
gcagagcatt acgctgactt gacgggacgg cgcaagctca tgaccaaaat cccttaacgt    2580
gagttacgcg tcgttccact gagcgtcaga ccccgtagaa aagatcaaag gatcttcttg    2640
agatcctttt tttctgcgcg taatctgctg cttgcaaaca aaaaaaccac cgctaccagc    2700
ggtggtttgt ttgccggatc aagagctacc aactcttttt ccgaaggtaa ctggcttcag    2760
cagagcgcag ataccaaata ctgttcttct agtgtagccg tagttaggcc accacttcaa    2820
gaactctgta gcaccgccta catacctcgc tctgctaatc ctgttaccag tggctgctgc    2880
cagtggcgat aagtcgtgtc ttaccgggtt ggactcaaga cgatagttac cggataaggc    2940
gcagcggtcg ggctgaacgg ggggttcgtg cacacagccc agcttggagc gaacgaccta    3000
caccgaactg agatacctac agcgtgagct atgagaaagc gccacgcttc ccgaagggag    3060
aaaggcggac aggtatccgg taagcggcag ggtcggaaca ggagagcgca cgagggagct    3120
tccagggga aacgcctggt atctttatag tcctgtcggg tttcgccacc tctgacttga    3180
gcgtcgattt ttgtgatgct cgtcaggggg gcggagccta tggaaaaacg ccagcaacgc    3240
ggccttttta cggttcctgg ccttttgctg gccttttgct cacatgttaa aaggccatcc    3300
gtcaggatgg ccttctataa aacgaaaggc ccagtcttcc gactgagcct ttcgttttat    3360
caaataatga ttttattttg actgatagtg acctgttcgt tgcaacacat tgatgagcaa    3420
tgcttttta taatgccaac tttgtacaaa aaagcaggct tttgtacaaa aaagcaggct    3480
acaccatggc tccaaagaag aagcgtaagg taatggtgag caagggcgag gaggacaaca    3540
tggccatcat caaggagttc atgcgcttca aggtgcacat ggagggctcc gtgaacggcc    3600
gcgagttcga gatcgagggc gagggcgagg ccgcccccta cgagggcacc cagaccgcca    3660
agctgaaggt gaccaaggc ggccccctgc ccttcgcctg gacatcctg tccctcagt    3720
tcatgtacgg ctccaaggcc tacgtgaagc accccgccga catccccgac tacttgaagc    3780
tgtccttccc cgagggcttc aagtgggagc gcgtgatgaa cttcgaggac ggcggcgtgg    3840
tgaccgtgac ccaggactcc tccctgcagg acggcgagtt catctacaag gtgaagctgc    3900
gcggcaccaa cttcccctcc gacggccccg taatgcagaa gaagaccatg ggctgggagg    3960
cctcctccga gcggatgtac cccgaggacg gcgccctgaa gggcgagatc aagcagaggc    4020
tgaagctgaa ggacggcggc cactacgacg ccgaggtcaa gaccacctac aaggccaaga    4080
```

```
agcccgtgca gctgcccggc gcctacaacg tcaacatcaa gctggacatc acctcccaca   4140
acgaggacta caccatcgtg aacagtacg agcgcgccga gggccgccac tccaccggcg    4200
gcatggacga gctgtacaag taagacccag cttctcttgta caaagtatgg ctccaaagaa  4260
gaagcgtaag gtaatggtga gcaagggcga ggaggacaac atggccatca tcaaggagtt   4320
catgcgcttc aaggtgcaca tggagggctc cgtgaacggc cacgagttcg agatcgaggg   4380
cgagggcgag ggccgcccct acgagggcac ccagaccgcc aagctgaagg tgaccaaggg   4440 cggcccctg cccttcgcct gggacatcct gtcccctcag ttcatgtacg gctccaaggc    4500
ctacgtgaag caccccgccg acatccccga ctacttgaag ctgtccttcc ccgagggctt   4560
caagtgggag cgcgtgatga acttcgagga cggcggcgtg gtgaccgtga cccaggactc   4620
ctccctgcag gacggcgagt tcatctacaa ggtgaagctg cgcggcacca acttcccctc   4680
cgacggcccc gtaatgcaga gaagaccat gggctgggag gcctcctccg agcggatgta    4740
ccccgaggac ggcgccctga agggcagat caagcagagg ctgaagctga aggacggcgg    4800
ccactacgac gccgaggtca agaccaccta caaggccaag aagcccgtgc agctgccggg   4860
cgcctacaac gtcaacatca gctggacat cacctcccac aacgaggact acaccatcgt    4920
ggaacagtac gagcgcgccg agggccgcca ctccaccggc ggcatggacg agctgtacaa   4980
gtaaacccag cttcttgta caaagttggc attataagaa agcattgctt atcaatttgt     5040
tgcaacgaac aggtcactat cagtcaaaat aaaatcatta tttgtacgac tcactatagg   5100
ggatcaggaa acagctatga catgagccat attcaacggg aaacgtcgag gccgcgatta   5160
aattccaaca tggatgctga tttatatggg tataaatggg ctcgcgataa tgtcgggcaa   5220
tcaggtgcga caatctatcg cttgtatggg aagcccgatg cgccagagtt gtttctgaaa   5280
catggcaaag gtagcgttgc caatgatgtt acagatgaga tggtcagact aaactggctg   5340
acggaattta tgcctcttcc gaccatcaag catttttacc gtactcctga tgatgcatgg   5400
ttactcacca ctgcgatccc cggaaaaaca gcattccagg tattagaaga atatcctgat   5460
tcaggtgaaa atattgttga tgcgctggca gtgttcctgc gccggttgca ttcgattcct   5520
gtttgtaatt gtccttttaa cagcgatcgc gtatttcgtc tcgctcaggc gcaatcacga   5580
atgaataacg gtttggttga tgcgagtgat tttgatgacg agcgtaatgg ctggcctgtt   5640
gaacaagtct ggaaagaaat gcataaactt ttgccattct caccggattc agtcgtcact   5700
catggtgatt tctcacttga taaccttatt tttgacgagg ggaaattaat aggttgtatt   5760
gatgttggac gagtcggaat cgcagaccga taccaggatc ttgccatcct atggaactgc   5820
ctcggtgagt tttctccttc attacagaaa cggcttttc aaaaatatgg tattgataat    5880
cctgatatga ataaattgca gtttcatttg atgctcgatg agttttcta acccgtagaa    5940 aagatcaaag gatcttcttg agatcctttt tttctgcgcg taatctgctg cttgcaaaca   6000 aaaaaccac cgctaccagc ggtggtttgt ttgccggatc aagagctacc aactctttt     6060 ccgaaggtaa ctggcttcag cagagcgcag ataccaaata ctgttcttct agtgtagccg    6120
tagttaggcc accacttcaa gaactctgta gcaccgccta catacctcgc tctgctaatc    6180
ctgttaccag tggctgctgc cagtggcgat aagtcgtgtc ttaccgggtt ggactcaaga    6240
cgatagttac cggataaggc gcagcggtcg ggctgaacgg ggggttcgtg cacacagccc    6300
agcttggagc gaacgaccta caccgaactg agatacctac agcgtgagct atgagaaagc    6360
gccacgcttc ccgaagggag aaaggcggac aggtatccgg taagcggcag gtcggaaca     6420 ggagagcgca cgagggagct tccagggga aacgcctggt atctttatag tcctgtcggg     6480
```

```
tttcgccacc tctgacttga gcgtcgattt ttgtgatgct cgtcaggggg gcggagccta    6540
tggaaaaacg ccagcaacgc ggccttttta cggttcctgg cctttttgctg gccttttgct  6600 cacat                                                                6605
```

TRANSPARENT ZEBRAFISH AND PREPARATION METHOD THEREOF

FIELD OF THE INVENTION

This invention relates to a method for preparing transparent zebrafish. This invention also relates to a novel transparent zebrafish.

BACKGROUND OF THE INVENTION

Zebrafish (*Danio rerio*) is a small tropical freshwater fish, and belongs to the family of Cyprinidae. They live in clean ponds in fields, and origins from the East India Ganges River valley, including Pakistan, India, Nepal and Bangladesh area. The appearance of their body has silver color as the background, and topped with blue stripes extending from head to tail; this is the main reason why they are called "zebra" fish. The average of the fish's body length is between 3 and 5 cm. Generally, the adult male body is slender and more yellowish in color; the adult female has more silver in color and the female body size is bigger with the extended abdomen containing oocysts inside. Zebrafish grow up from the fertilized egg to reproductive adulthood in about 3 months, and their average life is about 2 to 3 years. In nowadays, zebrafish is a popular aquarium fish, frequently admired by their body's shiny silver, blue and white stripes that scatters reflected bright light occasionally. The typical aquariums sell not only the wild typed strains, but also some special variant strains, such as the long tail fin zebrafish, golden zebrafish, leopard zebrafish and many other mutant varieties.

Outside the hobbyist's aquarium, zebrafish is also a popular model organism in biomedical research. Researchers used zebrafish to study developmental biology, revealing the functions of specific genes during development; zebrafish can also be used as human disease models to simulate various disease processes. The zebrafish model organism takes the biggest advantage of their "transparent" body during embryonic stage; it can provide live images for real-time observations, allowing researchers to clearly monitor the whole process of pathogenesis. However, the characteristic "transparent" appearance in zebrafish is limited only in early embryonic stage; with the individual growth, pigment cells would gradually cover the whole skin, and eventually obstruct direct observation, which is inconvenient for researchers. If technically, the transparent body can be maintained into the adult stage, it will be a major advantage to expand research capacity. Furthermore, adult animals present biological conditions closer to the true situations of a variety of disease models. After all, the zebrafish embryo represents the earliest stage of life and is a unique model, with many of their physiological mechanisms and organ functions different from the adult ones. Their small size also presents restrictions for some experimental manipulation, such as surgical operations.

At the late 1960s, Prof George Streisinger at the University of Oregon introduced zebrafish into the research laboratory and academic community. He described the developmental process in zebrafish, and defined the various developmental stages in detail. Such knowledge is useful for other researchers as references. Since then, zebrafish began to be widely used in developmental biology research. Being a favorable model organism, zebrafish possess many advantages: the maintenance costs are cheaper compared with other vertebrate model organisms such as mice or monkeys. In addition, zebrafish engage in courtship and spawn in the morning, so researchers can artificially manipulate light cycle to control the mating behavior of the zebrafish; furthermore, healthy female can lay a batch of about 200 to 300 eggs each time, which are enough to provide sufficient experimental materials and statistically significant sample size. Most important of all, the transparent zebrafish embryo is developed outside of the mother (i.e. not in the womb), which allows real time observation. Finally, zebrafish and mammals are all grouped in the chordate phylum, and thus have similar physiological features such as closed-type blood reservoir and circulation system, and congenital and acquired immune system. Zebrafish also possess many homologous organs similar to mammals, such as brain, heart, liver, pancreas, kidney, gastrointestinal tract, etc. These physiological characteristics are difficult to be completely owned in other simpler model organisms.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

This invention provides a novel transparent zebrafish and preparation method thereof. The transparent zebrafish is characterized by color analysis of image relative to wild type zebrafish, with an increase of 20-30% in red component percentage and a decrease of 20-30% in blue component percentage. The transparent zebrafish is also characterized by transparent and yellowish in appearance and uniformly pigmented black eyes. Inner organs of the transparent zebrafish are observable by eyes.

This invention also provides a method for in vivo observation of progression and expansion of various disease stages or physiological processes.

DETAILED DESCRIPTION OF THE INVENTION

Figure 1:
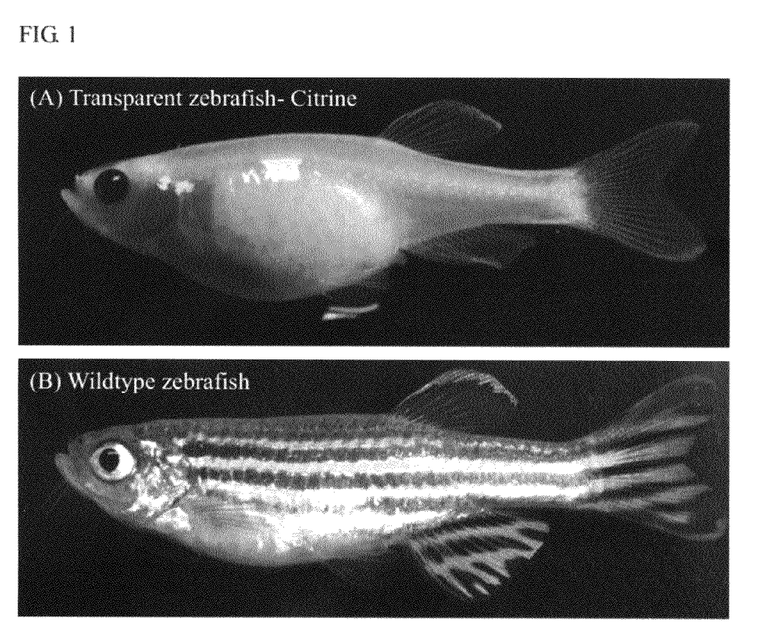
FIG. 1 shows the difference between a novel transparent zebrafish—Citrine (FIG. 1A) and a wild type zebrafish (FIG. 1B).
Figure 2:
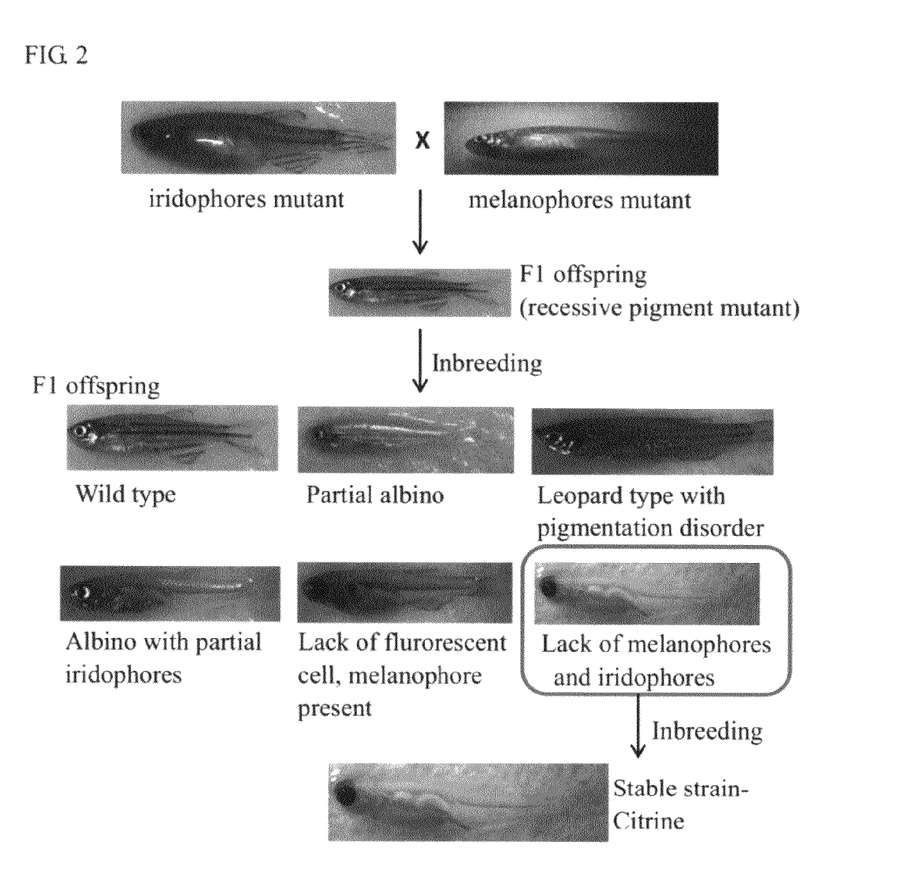
FIG. 2 shows the biological selective breeding technique in preparation of a novel transparent zebrafish—Citrine.

The present invention demonstrated the use of a biological selective breeding technique in preparation of a new line of transparent zebrafish—Citrine (FIG. 1). The present invention provides a method for preparation of transparent zebrafish, comprising: (1) using one mutant line of zebrafish which lacks iridophores and another mutant line which lacks melanophores as parent fish to produced offspring F0 (zero generation, recessive pigment mutant fish); (2) inbreeding F0 with F0 to obtain offspring F1; (3) selecting mutant fish which lacks both melanophores and iridophores from the offspring F1; and (4) inbreeding selected zebrafish of step (3) to obtain a next filial generation (FIG. 2).

Figure 3:
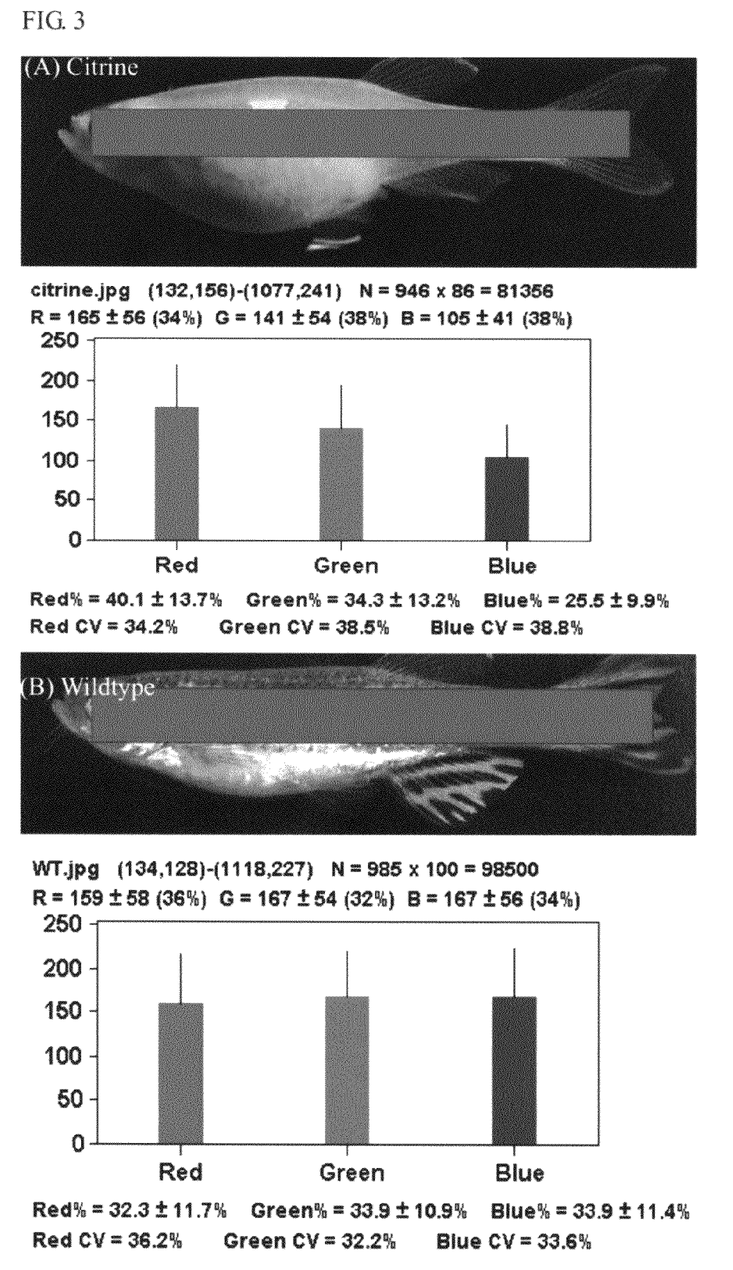
FIG. 3 shows the RGB color analysis of Citrine (FIG. 3A) and wild type zebrafish (*Danio rerio*) (FIG. 3B)

The new line of zebrafish, Citrine, prepared by the above method is characterized by lack of the pigment cells, including melanophores and iridophores, possessing only a small amount of xanthophores in their skin. Citrine is characterized by color analysis of image relative to wild type zebrafish, with an increase of 20-30% in red component percentage and a decrease of 20-30% in blue component percentage (FIG. 3). The appearance of Citrine is transparent and yellowish. Inner organs of Citrine are observable by eyes. Due to loss of iridophore, Citrine has uniformly pigmented black eyes. (i.e. loss the scleral iridophore layer around the eyes). The Zebrafish Citrine sperm had been deposited in CCTCC (China Center for Type Culture Collection) which belongs to International Depository Authority (IDA) under the Budapest Treaty is located at College of Life Sciences, Wuhan University, Wuhan 430072, China with deposit number of CCTCC C2013167. The deposit of CCTCC C2013167 was received on Jan. 8, 2014 and the viability of the deposited microorganism was tested on Jan. 17, 2014 and was tested to be viable.

Actually, there are many kinds of mutations of zebrafish which possess different defects in pigment related genes; people can purchase the mutations in the aquarium or conservation agencies, such as gold zebrafish—Golden, white zebrafish—Albino, etc., which all have different types and degrees of genetic pigmentation defects. At present, by molecular biology and genetics technology (ex. genotyping), the research community did identify some mutant genes and correlated these genes to the specific phenotypes caused by the mutation. However, there are many gene-mutation correlations remains to be identified.

Generally, pigment cells in fish are classified into three major categories: melanophore, xanthophore, and iridophore. Melanophores are black pigment cells and represent the dense black spots and lines in their skin; xanthophores are yellow pigment cells; iridophores compose the majority of the body colors. Crystal plates composed of guanine inside the iridophores scatter and reflect light, and thus generate the shiny color in skin of the fish. Briefly speaking, most of the brilliant colors of the fish seen by our eyes are coming from reflection of light in iridophores (Rawls J F et al., *Dev Biol* 2001, Vol. 240(2): 301-314).

The transparent zebrafish of the present invention, Citrine, lacks black melanophores and reflective iridophores, leaving only few yellow xanthophores, in their skin; hence, the appearance of Citrine is yellowish. The transparent phenotype of Citrine is expressed from embryo to adult. The transparency of skin allows direct observation of organs inside Citrine, including brain, heart, liver, gastrointestinal tract, swim bladder, ovary and many other organs. As presented here, Citrine is a novel line of transparent zebrafish, and is quite different from other mutant lines. There is another transparent zebrafish line, Limid zebrafish (AZOO, Taiwan), available in the aquarium market. AZOO transparent zebrafish lacks melanophores but still possesses some iridophores, so one can observe reflective iridophores in its lower abdomen and around the eyes (i.e. scleral iridophore layer). The iridophores around the eyes are obvious distinction between Citrine and AZOO transparent zebrafish. In 2008, the research team at Children's Hospital in Boston (USA) generated a transparent fish, Casper, which also lacks the pigment cells, melanophores and iridophores. (White R M et al, *Cell Stem Cell* 2008, Vol. 2(2):183-189) Citrine is different from Casper for two reasons: (1.) Citrine and Casper are generated from totally different parental and maternal fish lines and hence their genomic makeup are totally different. Although they have similar defects in some apparent phenotypes such as melanophores and iridophores defects, there must be many recessive and different phenotypes caused by their totally different genomic background. (2.) In the appearance, Citrine looks more yellowish when compared with Casper. In other word, the degrees of xanthophore deposition are obviously different.

To describe in detail, the present invention not only can be applied in ornamental purposes, but also have great potential to become a new type of tools in biomedical research. The present invention is expected to bring many breakthroughs in biomedical research, particularly real time in vivo imaging. Citrine possesses similar vital organs and comparable physiology with the higher vertebrates; combining with its transparent body, Citrine is suitable to be used in creating various disease models. The present invention provides a method for in vivo observation of progression and expansion of various disease stages or physiological processes, comprising (1) introducing cell or agent into the transparent zebrafish of the present invention and (2) observing progression and expansion or physiological process of target cell or organ. The cell or agent is selected from tumor cell, stem cell, mutant cell, disease causing agent, and pharmaceutical composition. The progression and expansion of various disease stages or physiological processes, including tumor graft, cancer metastasis, stem cell transplantation, angiogenesis, cardiovascular diseases, aging, behavior pattern, obesity, drug screening, infection, tissues regeneration, body color or pigment related genes identification, melanoma cell transplantation, and internal organs observation. The transparent zebrafish of the present invention is also applied to screening an agent for a pharmacological activity in vivo. For the implementation of the cases mentioned, the transparent zebrafish of the present invention, Citrine, is obtained as described.

The examples below are non-limiting and are merely representative of various aspects and features of the present invention. The transparent zebrafish of the present invention, Citrine is applied in establishment of tumor xenograft model (Langenau D M et al., *Science* 2003, Vol. 299 (5608): 887-890), cancer metastasis (Amatruda J F et al., *Cancer Cell* 2002, Vol. 1 (3): 229-231), stem cell transplantation (Traver D et al., *Nat Immunol* 2003, Vol. 4 (12): 1238-1246), angiogenesis (Nicoli S et al., *Cancer Res* 2007, Vol. 67 (7): 2927-2931), cardiovascular diseases (Chico T J et al., *Trends Cardiovasc Med* 2008, Vol. 18 (4): 150-155), aging studies (Kishi S et al., *Exp Gerontol* 2003, Vol. 38 (7): 777-786), behavioral studies (Cachat J et al., *Nat Protoc* 2010, Vol. 5 (11): 1786-1799), obesity (Song Y et al., *FASEB J* 2007, Vol. 21 (9): 2042-2049), drugs screening (Tran T C et al., *Cancer Res* 2007, Vol. 67 (23): 11386-11392, Eimon P M et al., *Expert Opin Drug Metab Toxicol* 2009, Vol. 5 (4): 393-401), immunity and infection (Davis J M et al., *Cell* 2009, Vol. 136 (1): 37-49), and the regeneration of various organs, including neuron regeneration (Byrd C A et al., *Neuroscience* 2001, Vol. 105 (4): 793-801), spinal cord regeneration (Hui S P et al., *Dev Dyn* 2010, Vol. 239 (11): 2962-2979), retinal regeneration (Vihtelic T S et al., *J Neurobiol* 2000, Vol. 44(3): 289-307), heart regeneration (Poss K D et al., *Science* 2002, Vol. 298 (5601): 2188-2190), caudal fin regeneration (Poleo G et al., *Dev Dyn* 2001, Vol. 221 (4): 380-390).

The transparent zebrafish of the present invention, Citrine, which lacks pigment cells, melanophores and iridophores, for example but not limitation, is used for body color or pigment related genes identification, and melanoma cell transplantation. (Haldi M et al., *Angiogenesis* 2006, Vol. 9 (3): 139-151).

The transparent zebrafish of the present invention, Citrine, is applied to observe the internal organs in vivo, for example but not limitation, including: brain, eyes, spinal cord, heart, liver, gastrointestinal tract, kidney, reproductive system; based on this characteristic, some disease processes such as brain trauma, stroke, retinal vascular proliferation, spine trauma, heart failure, myocardial infarction, cardiac arrhythmia, liver cirrhosis, liver damage, abnormal gastrointestinal motility, colon cancer, kidney failure, reproductive system, infertility research, etc.

The transparent zebrafish of the present invention, Citrine, for example but not limitation, is used to create novel transgenic zebrafish which expresses fluorescent proteins in specific organs for tissue label. The transgenic zebrafish further implants other genes to create various mutant lines. Citrine is a novel research tool or founder to generate popular ornamental fish.

EXAMPLES

The examples below are non-limiting and are merely representative of various aspects and features of the present invention.

Example 1

Preparation of Transparent Zebrafish

Materials (1) Spontaneous mutant line which lacks iridophores—Pink Lady
(2) Commercial mutant line which lacks melanophores—AZOO transparent zebrafish (AZOO, Taiwan).

Figure 7:
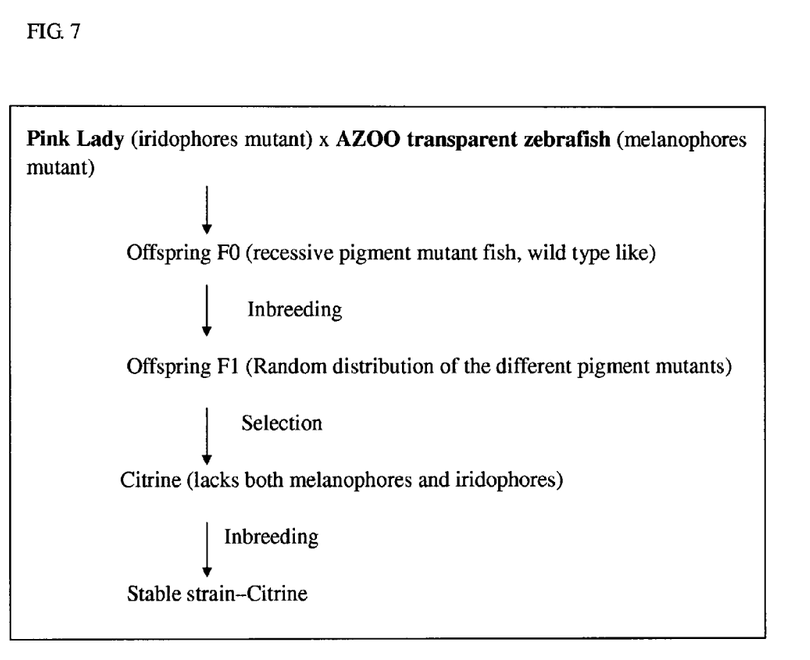
FIG. 7 shows the flow chart of preparation of transparent zebrafish.

Flow chart is shown in FIG. 7 (as shown in FIG. 2):
1. The mutant line, Pink Lady, was mated with another mutant, AZOO transparent zebrafish to obtain offspring F0 which were recessive pigment mutant fish and wild type like.
2. The offspring F0 were inbreeded to obtain the offspring F1 which was composed of a pool of mutant fish with random distribution of pigment defects.
3. The mutant fish which lacks both melanophores and iridophores was selected, and named as Citrine.
4. Citrine was inbreeded to obtain their next generation and the phenotype of Citrine could be passed to their offspring constantly was confirmed.

The mutant line, Pink Lady, is a spontaneous mutant line which is characterized by overall lack of iridophores, and the uniformly pigmented black eyes without scleral iridophore layer, but Pink Lady still possess many melanophores. A commercially available mutant line, AZOO transparent fish, which is obviously a melanophore mutant, was mated with Pink Lady to perform biologically selective breeding.

After mating the mutant line, Pink Lady, with AZOO transparent zebrafish, the offspring generation F0 was obtained; which processed recessive mutant genes with the phenotypes the same with normal wild-type zebrafish. According to basic principles of genetic inheritance: Mendel's law, the offspring from such cross breeding would obtain half of its genome from its parental line and another half from its maternal line. Thus, offspring F0 obtained half of the normal melanophores gene from Pink Lady and half of the normal iridophores gene from AZOO transparent zebrafish; since the wild-type genes are dominant over the mutant genes, offspring F0 would carry the recessive mutant genes and display the normal phenotypes.

After rearing the recessive mutant offspring F0 for 3 month, the offspring F0 reached sexual maturity. By inbreeding the offspring F0, the next offspring generation F1 were obtained; interestingly, the phenotypes (variations of appearances) of the offspring F1 were a range of the combination of various pigment gene mutations. A pool of zebrafish mutants with random distribution of pigmentation was generated, as seen in changes of stripe patterns and colors. Only the one lacking both melanophores and iridophores was selected and conducted breeding again, which eventually led to the generation of the rare ones with desired transparent phenotype, Citrine.

Similarly, rearing the selected Citrine for 3 month, Citrine reached sexual maturity. By inbreeding Citrine, the featured phenotype—"one lacking both melanophores and iridophores in the skin" passed to their offspring was validated. If so, it indicates that this mutant line is stable: the new mutant line, Citrine was successfully created.

Example 2

Color Analysis

Since it is abstract to depict the color pattern and transparency of Citrine, the RGB color analysis software (RGB software, Byers J A, *Ann Entomol Soc Am* 2006, Vol. 99 (5): 865-874) was applied to measure the red, green, and blue (RGB) intensity components of the pixels in specified area (as shown in FIG. 3) of Citrine image for quantitative comparison with that of wild typed zebrafish (*Danio rerio*). The result is listed in Table 1.

TABLE 1

| | Color percentages | | |
|---|---|---|---|
| | Red | Green | Blue |
| Citrine | 40.1 ± 13.7% | 34.3 ± 13.2% | 25.5 ± 9.9% |
| Wild type | 32.3 ± 11.7% | 33.9 ± 10.9% | 33.9 ± 11.4% |

The relatively higher percentage of red color in Citrine is correlated to its transparency: loss of reflective iridophores allows direct observation of the red blood and circulation vessels in trunk and gill. The relatively lower percentage of blue colors is also due to loss of iridophores, correlating to the lack of brilliant blue stripes in the body.

Example 3

Live Organ Observation

Figure 4:
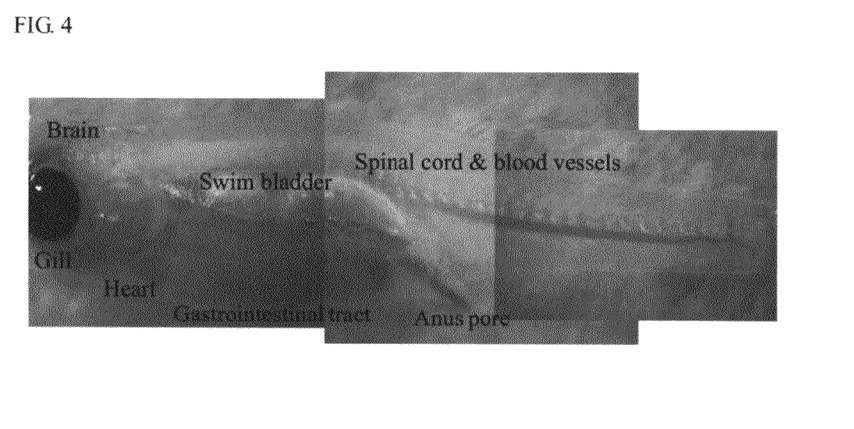
FIG. 4 shows in vivo organ observation of the transparent zebrafish—Citrine, including brain, spinal cord, blood vessels, gill, heart, liver, gastrointestinal tract, swim bladder and anus pore.

The transparent characteristic of Citrine zebrafish allows researchers to observe live organs in real time. After anesthesia, Citrine was put under the stereo microscope to allow direct observation of its organs in vivo. As shown in FIG. 4, researchers may see all the organs, including brain, spinal cord, blood vessels, gill, heart, liver, gastrointestinal tract, swim bladder and anus pore.

Example 4

Heart Specific Transgenic Fluorescent Zebrafish

Figure 5:
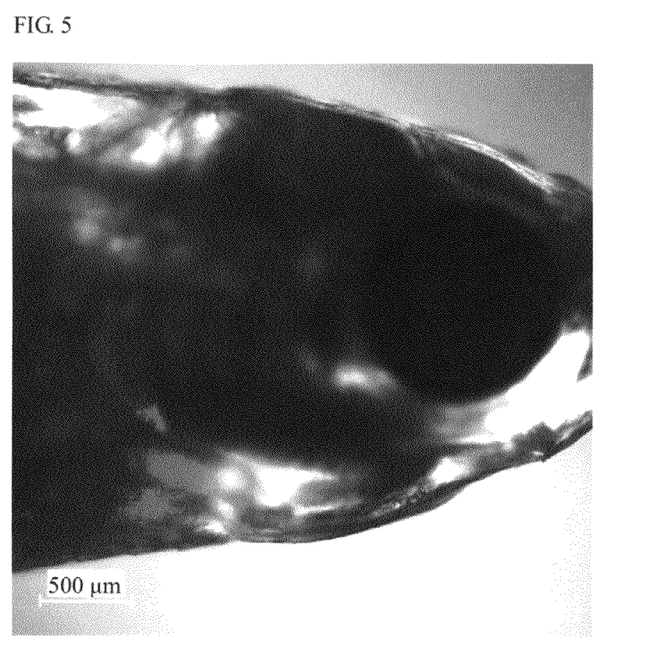
FIG. 5 shows the beating red fluorescent heart of the heart specific transgenic fluorescent transparent zebrafish under fluorescence microscope.

In the embodiment of the present invention, a transgenic fluorescent zebrafish, Tg (cmlc2-nls-mCherry) in Citrine was created. First, the promoter sequence (−875_690) of a cardiac specific gene, cmlc2 (cardiac myosin light chain II) (SEQ ID NO: 1) was cloned, which is used to drive the expression of a fluorescent reporter gene, nls-mCherry (pME-nls-mCherry, SEQ ID NO: 2). This vector was then microinjected into the embryos of Citrine. After selecting for the stable line, the transgenic Citrine with the red fluorescent heart—Tg (cmlc2-nls-mCherry) was obtained. With it, the beating red fluorescent heart of adult object could be observed (FIG. 5). It also can be used to study the cardiovascular physiology under fluorescence microscope directly due to its transparent body.

Example 5

Vasculature Specific Transgenic Fluorescent Zebrafish

Figure 6:
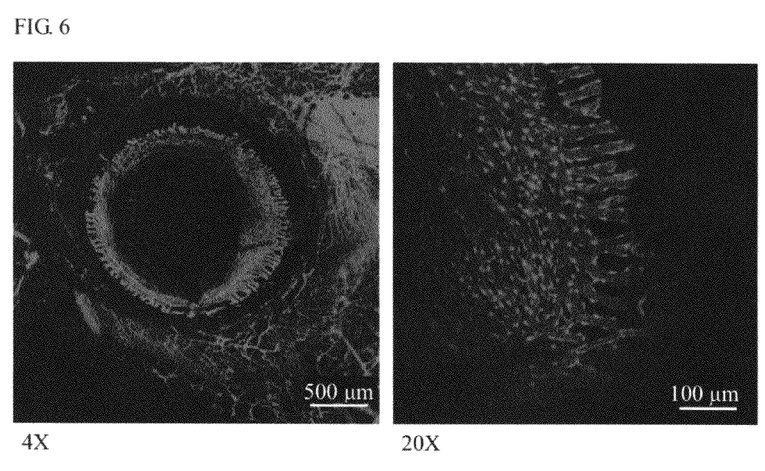
FIG. 6 shows a transgenic zebrafish with green fluorescent protein expressed only in the vasculatures under fluorescence microscope.

Citrine was mated with a commercially available green fluorescent blood vessel zebrafish (ZIRC, Catalog ID: ZL1197), Tg (kdrl: EGFP) s843. KDR stands for Kinase insert Domain Receptor, it is a gene expressed specifically in the vasculatures. After breeding and selection, a new transgenic zebrafish line with green fluorescent protein expressed only in the vasculatures of Citrine zebrafish was obtained. Because of the lack of scleral iridophore layer in the eyes of Citrine, the blood vessels of the eyes could clearly be seen under fluorescence microscope (FIG. 6). It can be used to study retinal vascular biology and the related diseases.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A transparent Citrine zebrafish whose genome comprises AZOO transparent zebrafish and pink lady mutations, which is characterized as having an increase of 20-30% in red component percentage and a decrease of 20-30% in blue component percentage relative to wild type zebrafish, inner organs being visible, yellow pigments on dorsal skin, and transparent phenotype expressed from embryo to adult.

* * * * *